United States Patent [19]

Strader

[11] Patent Number: 4,722,218

[45] Date of Patent: Feb. 2, 1988

[54] DEVICE FOR MEASUREMENT OF COEFFICIENT OF FRICTION

[75] Inventor: Don S. Strader, Uniontown, Ohio

[73] Assignee: The Goodyear Tire & Rubber Company, Akron, Ohio

[21] Appl. No.: 910,034

[22] Filed: Sep. 22, 1986

[51] Int. Cl.[4] ............................................. G01N 19/02
[52] U.S. Cl. ................................................... 73/9
[58] Field of Search .................. 73/9, 7, 8, 763, 760, 73/767, 774

[56] References Cited

U.S. PATENT DOCUMENTS

| 2,821,081 | 1/1958 | Staples | 73/9 |
| 4,315,426 | 2/1982 | Brandon | 73/9 |

FOREIGN PATENT DOCUMENTS 436249 10/1974 U.S.S.R. ................................. 73/9

Primary Examiner—Stewart J. Levy
Assistant Examiner—Robert R. Raevis
Attorney, Agent, or Firm—M. R. Dion, Sr.

[57] ABSTRACT

There is disclosed a portable apparatus (10) for measuring relative coefficients of friction of a cnoveyor belt (12) or other work surface. A rounded contact shoe (38) contacts the surface while suspended between two flanking wheels (18,20). The shoe (38) forms one end of a lever arm (68) which is variably spring loaded at the opposite end to constantly urge the shoe (38) into contact with the moving test surface (42). The relative resistance is measured by a detector means, such as a load cell or strain gage (44) mounted in connection with the lever arm (68).

11 Claims, 3 Drawing Figures

DEVICE FOR MEASUREMENT OF COEFFICIENT OF FRICTION

BACKGROUND OF THE INVENTION

This invention relates generally to devices for measuring the coefficient of friction of a work surface, and in particular to a device adapted for measuring the coefficient of friction of a moving conveyor belt.

Overland conveyor belts for mining installations may have belts in excess of two miles in length. In order to efficiently convey loads, the belts must travel in the desired path and must form a suitable trough on the rollers of the conveying system. There is some tendency for some belts, particularly cable-type belts, to vary their path over the length of the conveying distance. This tracking variation is undesirable in that the troughing cross section of the belt changes as it moves off center in the conveyor apparatus. This movement damages the edge of the belt, the supporting frame and spills payload. A testing device was needed to determine in the field what the coefficient of friction was for the belt over its entire length and width. This required an instrument which was mobile enabling it to be set up conveniently in the field. It also must be reliable in being able to report relative frictional coefficients for the various portions of the belt being tested. The ability to accurately measure relative coefficient of friction over the length and width of the belt might enable the belt designer and conveyor system designer to work together to achieve a belt which tracks in a consistently straight line without the assistance of expensive training idlers on the conveyor system.

An object of the invention is to provide a compact, simple and reliable instrument for measuring coefficient of friction of a work surface, particularly a rubber or plastic conveyor belt. The design must be durable and produce consistent and reproducible results over a variety of belt surface conditions. The advantage of the invention described herein is that a simple yet reliable instrument can be field installed on a conveyor to obtain relative coefficient of friction for further analysis.

BRIEF DESCRIPTION OF THE INVENTION

An embodiment of the invention is an apparatus for measuring the coefficient of friction of a work surface comprising a handle having a slot extending medially therein; a pair of substantially hemispheric wheels spaced axially apart on and mounted to a shaft journaled in one end of said handle; a feeler pivotally mounted non-concentrically on a pivotal pin which is non-concentric with said shaft for mounting said pair of wheels, said feeler having a contact head portion positioned medially between said pair of wheels and a lever arm portion extending into said slot in said handle and restrained from touching said slot by a pin which limits the rotational movement of said lever arm within said slot; a plurality of bores extending perpendicularly with said lever arm through said handle, said bores being spaced apart along said lever arm and lying within an imaginary plain established by the rotational movement of said feeler about said rotational pin, at least one of said bores containing a spring extending into said slot and contacting said lever arm, said spring being constrained from axial movement within the bore at the end distal of the lever arm, said spring exerting a constant force on said lever arm; a strain gauge composed of opposing arrays of fine wires set on opposite sides of said feeler, said wires exhibiting electrical resistance which varies directly with the degree of extension of said wires.

The simplest form of the invention is an apparatus for measuring the coefficient of friction of the surface comprising a handle having a slot extending medially therein; a pair of rotatable wheels mounted and spaced axially apart on a shaft rotatably connected to one end of said handle; a feeler, pivotally mounted on a pivotal mounting means rigidly attached to said one end of said handle and extending medially between said pair of wheels through said slot in said handle, said feeler having a contact head portion positioned medially between said pair of wheels and a lever arm portion extending into said slot in said handle; a means for exerting a constant force on said lever arm portion of said feeler for spring biasing said contact head portion in an enlargement made with said surface; and a strain-sensing means attached to said feeler for sensing a force exerted on said contact head portion of said feeler by said surface as it passes over said contact head portion of said feeler.

DETAILED DESCRIPTION OF THE INVENTION

Figure 1:
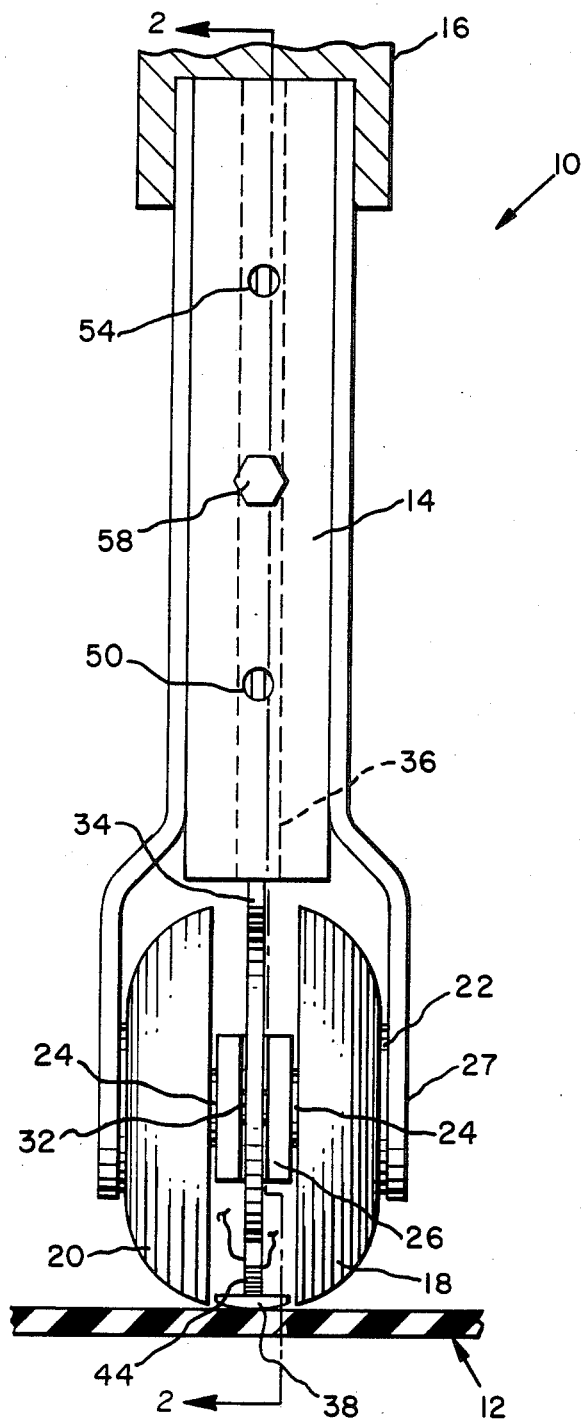
FIG. 1 is a front elevational view of the apparatus for measuring coefficient of friction of a conveyor belt.
Figure 3:
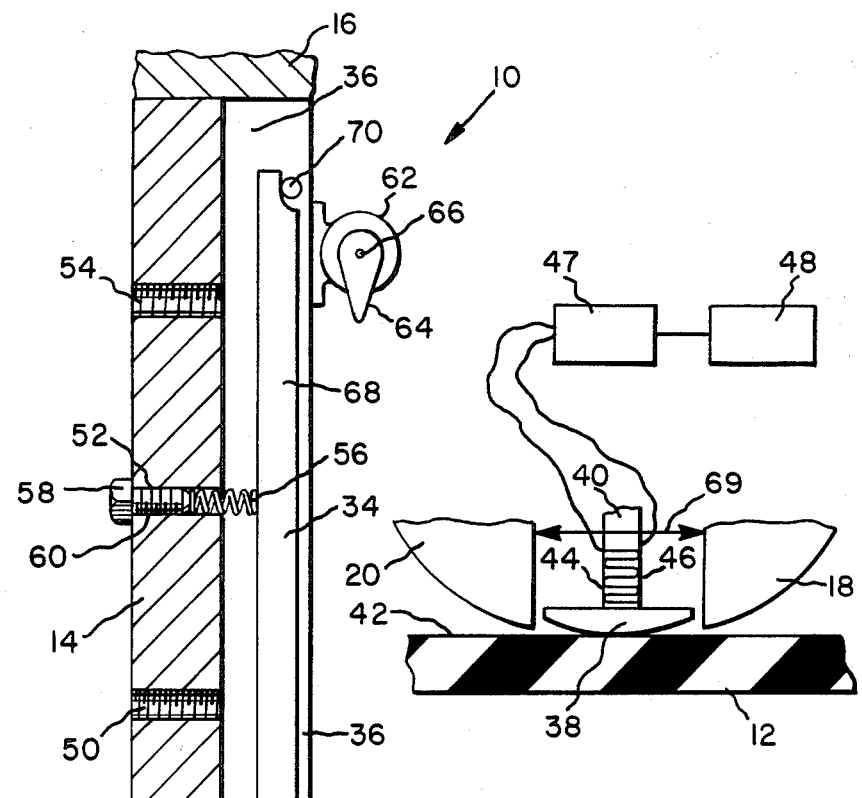
FIG. 3 is a partial sectional view of the apparatus and belt of FIG. 2 taken along line 3—3.
Figure 2:
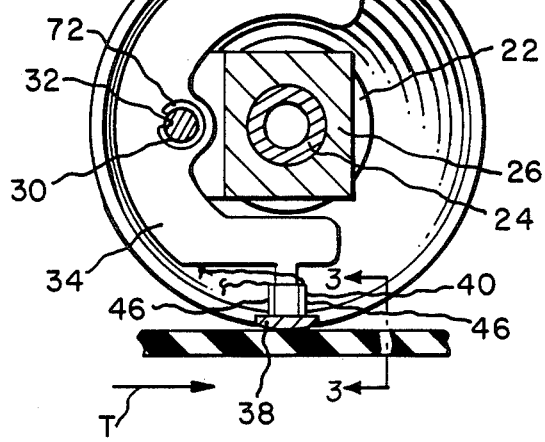
FIG. 2 is a sectional view of the apparatus of FIG. 1 taken along line 2—2.

FIGS. 1, 2 & 3 illustrate the preferred form of the apparatus 10 which measures the coefficient of friction of a moving surface. One particularly useful application is in measurement of the coefficient friction at various places on a rubber conveyor belt 12. It is particularly useful to determine whether the coefficient of friction varies across the belt longitudinally or transversely of its direction of travel. The coefficient of friction is believed to influence the manner in which a large overland conveyor belt tracks on its guiding pulleys. The apparatus 10 consists of a handle 14 which may be either hand-held or preferably mounted on a suitable support means 16. Two generally hemispheric shaped wheels 18 and 20 are mounted on bearings 22 carried on shaft 24. The shaft 24 is fitted into a pair of flanges 27 which are a part of the handle 14. The clevis 26 contains a bore 30 through which a pin 32 is fixed. The pin 32 supports and provides a pivot point for a feeler 34 which extends along a slot 36 provided in the handle 14. Feeler 34 is basically a lever arm which includes a contact head 38 and a connecting shaft 40 attaching to the feeler 34. FIG. 3 best shows the detail of the contact head 38 as it contacts the belt surface 42. FIG. 2 shows the direction of travel T of the belt as frictional force from the belt surface 42 is transmitted thru the contact head 38 to a strain gauge 44 positioned around the connecting shaft 40.

The strain gauge 44 shown best in FIG. 3 is of conventional type which includes a series of very fine wires which are arranged in arrays on opposing sides of the member upon which the strain is being sensed. The differential resistances between the arrays 46 measures the minute deflection which results during stressing of the connecting shaft 40. The arrays 46 are positioned on the front and back of the connecting shaft 40. Front and back are relative to the direction T and may also be considered to be normal and perpendicular to the plane of the belt surface 42. Any suitable strain sensing means could be substituted for the strain gauge shown in FIGS. 2 and 3. One alternative form would involve having a load cell positioned directly adjacent to the feeler 34 such that small changes in displacement of the feeler 34 as it pivots around the pin 32 would be sensed by the load cell which was affixed to the clevis 26. Regardless of the sensing means used to determine the amount of stress being placed on the contact head 38, the output from the sensing means such as the strain gauge 44 is sent to a suitable detector means 47. The detector means 47 may be any known conventional means of detecting the electrical signals of the strain gauge 44 including a conventional meter or solid state detection device. Optionally the output from detector means may be sent to a suitable recorder 48 for temporary or permanent display of the output of the apparatus 10. The recording means 48 can be a strip chart recorder, a continuous digital readout, or any data gathering data storage mode for subsequent processing by manual or electronic means.

The handle 14 may be fitted with any suitable means for exerting biasing force on the feeler 34 which extends thru the slot 36 in the handle. This biasing force preferentially keeps the contact head 38 in the optimal orientation to the surface 42 despite the counteracting forces generated by the frictional drag of the belt 12 moving in direction T. A simple mechanical means of exerting that force is shown in FIG. 2 in which the handle 14 contains a series of bores 50, 52 and 54 into which a spring 56 may be inserted and positioned utilizing a threaded restraining bolt 58. The spring 56 contacts the feeler on one end and the bolt 58 on the other thereby exerting downward pressure on the feeler 34. The amount of force can be finely adjusted using the bolt 58 to adjust spring tension by rotating the bolt 58 within the complimentary threads 60 provided in the bore 52. More gross adjustments may be made by moving the spring 56 to either bore 50 thereby providing lesser downward pressure or bore 54 to provide greater downward pressure. This ability to provide variable amounts of force on the feeler 34 is necessary in order to have an apparatus 10 which may be utilized for extremely hard surfaces as well as very soft surfaces. As the coefficient of friction increases greater levels of force must be exerted by the spring 56 in order to maintain the contact head 38 in a centered position between the wheels 18 and 20 during use of the device.

When long duration measurements are being made on a long conveyor belt assembly, the heat build-up generated by the frictional contact between the contact head 38 and the belt surface 42 is substantial and can adversely affect the reliability of the output from the strain gauge 44 or any other sensing means utilized. Therefore, it may be desirable to release contact between the contact head 38 and belt 12 periodically in order to stabilize the heat build up over a long period of use. To that end, a simplified expedient is shown on FIG. 2 in which a small motor 62 is shown which carries a rotating cam 64. As the motor revolves around its axis 66 it periodically engages the cam 64 with the lever arm portion 68 of the feeler 34 and rotates the lever arm around the pivot point formed by the pin 32 thereby rotating the contact head out of contact with the belt surface 42. This position is maintained during the contact of the cam 64 with the lever arm portion 68 of feeler.

In operation the apparatus 10 is placed in contact with a moving surface or may be drawn across a stationary surface. The action of the contact head is biased toward a centered orientation by the spring force exerted on the lever arm 68. The force of the contact head against the belt surface 42 is independent of the force of the wheels 18 and 20 against the belt 12. The frictional force generated by the belt against the contact head can be accurately read by the strain gauge 44 at any condition.

The pair of wheels 18 to 20, when viewed in axial cross section preferably taper radially inward from the axis as you proceed axially outward. The most preferred form of the wheel is one in which the individual wheels each take substantially hemispheric shape as shown in FIG. 1. This spherical shape to the wheel is functionally significant. Application of progressively greater engagement force has a general tendency to bow the belt downward and outward away from the inner edge of the wheel. This bowing or bridging action, if substantial enough, will tend to move the belt surface 42 away from the contact head 38. However, if the hemispheric/spherical form of wheels is utilized, it can be seen that the tendency for the belt to bridge away from the contact head 38 will be minimized. If normal wheels having generally cylindrical shape were utilized, the belt would tend to ride on the outermost edge of the wheels, thus forming a trough and depriving the contact head 38 of continuous contact with the belt surface 42.

The contact head 38 is most preferably, in a generally hemispheric form and should have a radius which is large relative to the gap 69 between the wheels 18 and 20. This geometric form assures a tapering contact surface to the contact head 38 which will accommodate roughness in the belt's surface and still maintain sufficient contact with the belt surface. Other arcuate or tapering forms may also be envisioned which would be useful.

The bores 50, 52, 54 are spaced apart along the lever arm 68 and extend perpendicularly into the slot 36 in the handle 14. The bores are preferably oriented within the imaginary plane established by the unrestrained rotational movement of the lever arm 68 about the pivot point formed by the pin 32. This orientation of perpendicularity relative to the lever arm is desired in order to achieve consistent spring tension against the lever arm during operation. A pin 70 positioned within the slot 36 of the handle is one suitable configuration of a means for limiting the rotational movement of the lever arm 68. The positioning of the pin 70 provides a rotational limitation of the contact head 38 which is a portion of the feeler 34. It is easily appreciated that the pin 32 around which the feeler pivots should be fitted with suitable axially limiting stops 72 to assure that the contact head 38 remains spaced apart from the inner peripheral surface of the wheels 18 and 20. Any suitable means for assuring this positioning is within the scope of the invention.

Any conventional type of elastomeric belt, preferably reinforced with fabric or longitudinal steel cables are likely candidates for being improved by the use of this method. The term elastomeric encompasses all polymers conventionally used in belts. Representative elastomeric materials are natural and synthetic rubbers as well as thermo plastic polymers such as polyvinyl chloride, urethanes and thermoplastic elastomers. Blends and alloys of rubbers and plastics are also included.

Preferred embodiments of the invention have been shown and described for illustration purposes. It will now become apparent to those skilled in the art that various changes in the form and detail may be made without departing from the scope of the invention. Accordingly, the full scope of the invention is set forth in the following claims.

What is claimed is:

1. An apparatus for measuring the coefficient of friction of a work surface comprising:
   (a) a handle having a slot extending medially therein;
   (b) a pair of spaced apart wheels mounted to a shaft journaled in one end of said handle;
   (c) a feeler pivotally mounted non-concentrically on a pivotal pin which is non-concentric with said shaft for mounting said pair of wheels, said feeler having a contact head portion positioned medially between said pair of wheels and a lever arm portion extending into said slot in said handle and restrained from touching said slot by a pin which limits the rotational movement of said lever arm within said slot;
   (d) a plurality of bores extending perpendicularly to said lever arm through said handle, said bores being spaced apart along said lever arm and lying within an imaginary plain established by the rotational movement of said feeler about said pivotal pin, at least one of said bores containing a spring extending into said slot and contacting said lever arm, said spring being constrained from axial movement within the bore at the end distal of the lever arm, said spring exerting a constant force on said lever arm; and
   (e) a strain gauge composed of opposing arrays of fine wires set on opposite sides of said feeler, said wires exhibiting electrical resistance which varies directly with the degree of extension of said wires.

2. An apparatus for measuring the coefficient of friction according to claim 1 further comprising a detector means providing output, said detector means being electrically connected to said arrays of fine wires of said strain gauge for measurement of differential resistance between the arrays of wires positioned on opposite sides of said feeler.

3. An apparatus for measuring the coefficient of friction according to claim 2 further comprising a recording means connected to said detector means for recording the output from the detector means.

4. An apparatus for measuring the coefficient of friction of a surface comprising;
   (a) a handle having a slot extending medially therein;
   (b) a pair of rotating wheels mounted and spaced axially apart on a shaft rotatably connected to one end of said handle;
   (c) a feeler, pivotally mounted on a pivotal mounting means attached to said one end of said handle and extending medially between said pair of wheels through said slot in said handle, said feeler having a contact head portion positioned medially between said pair of wheels and a lever arm portion extending into said slot in said handle;
   (d) a means for exerting a constant force on said lever arm portion of said feeler for spring biasing said contact head portion into an engagement position with said surface being a plurality of spaced-apart bores extending through said handle into said slot, said bores being spaced apart along said lever arm and oriented perpendicular to said lever arm and parallel with an imaginary plane established by the rotational movement of said feeler about said pivotal mounting means, at least one of said bores containing a spring with a first and second end constrained on the first end by a means for limiting movement of the spring and the second end of said spring being compressed against said lever arm thereby creating the constant force for biasing said contact head in said engagement position with the surface;
   (e) a strain-sensing means attached to said feeler for sensing a force exerted on said contact head portion of said feeler by said surface as it passes over said contact head portion of said feeler.

5. An apparatus for measuring the coefficient of friction according to claim 4 wherein said wheels have a substantially hemispheric form, said wheels being spaced apart on said shaft such that the hemispheric wheels face each other across a gap.

6. An apparatus for measuring the coefficient of friction according to claim 5 wherein said contact head has the form of a partial sphere having a radius substantially greater than the axial dimension of the gap to assure a smooth movement of said surface under said contact head portion.

7. An apparatus for measuring the coefficient of friction according to claim 5 wherein said feeler is pivotally mounted such that the contact shoe portion of said feeler moves non-concentrically with respect to said shaft by a pin having means for limiting the axial movement of said feeler within said gap between said pair of wheels.

8. An apparatus for measuring the coefficient of friction according to claim 4 further comprising a means for limiting the rotational movement of said lever arm of said feeler about said pivotal mounting means.

9. An apparatus for measuring the coefficient of friction according to claim 4 wherein said strain sensing means is a strain gauge composed of opposing arrays of fine wires set on opposite sides of said feeler, said wires exhibiting electrical resistance which varies directly with the degree of extension of said wires.

10. An apparatus for measuring the coefficient of friction according to claim 4 further comprising a means for moving said contact head alternately into and away from contact with said surface.

11. An apparatus for measuring the coefficient of friction according to claim 10 wherein said means for moving said contact head is a motor-operated cam which during its rotational path alternately engages and disengages the lever arm portion of said feeler thereby pivoting said feeler about said pivotal mounting means and alternatively engaging and disengaging said contact head from said engagement position with said surface.

* * * * *